US00PP07767P

United States Patent [19]

Vlielander

[11] Patent Number: Plant 7,767

[45] Date of Patent: Jan. 14, 1992

[54] KALANCHOE PLANT — KIEBESSY CULTIVAR

[75] Inventor: Ike Vlielander, De Lier, Netherlands

[73] Assignee: Fides Beheer B.V., De Lier, Netherlands

[21] Appl. No.: 578,478

[22] Filed: Sep. 5, 1990

[51] Int. Cl.[5] ..... A01H 5/00
[52] U.S. Cl. ..... Plt./68
[58] Field of Search ..... Plt./68, 87.15

*Primary Examiner*—Howard J. Locker

*Attorney, Agent, or Firm*—Burns, Doane, Swecker & Mathis

[57] ABSTRACT

A new and distinct cultivar of Kalanchoe plant named Kiebessy is provided. The plant forms attractive bright pink flowers, exhibits a strong growth habit, and is freely branched. The plant is very floriferous, and is particularly well suited for growing as a colorful ornamental potted plant which brightens the environment. The keeping quality of the new cultivar is extremely good.

1 Drawing Sheet

SUMMARY OF THE INVENTION

The new variety of Kalanchoe plant was created at De Lier, The Netherlands, in a controlled environment by artificial pollination wherein two parents were crossed which previously had been studied in the hope that they would contribute the desired characteristics. The female parent (i.e., the seed parent) was the Vesuvius cultivar. The male parent (i.e., the pollen parent) was designed FK 84-127. Such unnamed FK 84-127 plant was formed by crossing the product of a cross between the Tijuana cultivar and an unnamed plant designated 83-0721 by the product of a cross between the Venus cultivar and the Sensation cultivar. The parentage of the new cultivar can be summarized as follows:

VESUVIUS × (TIJUANA × 83-0721) ×

(VENUS × SENSATION).

The seeds resulting from the above pollination were sown and small plantlets were obtained which were physically and biologically different from each other. Selective study resulted in the identification of a single plant of the new cultivar.

It was found that the new cultivar of the present invention can be readily distinguished from its Vesuvius parent cultivar through the exhibition of an attractive bright pink flower coloration, a stronger growth habit, a larger leaf size, and a superior keeping quality.

It has been found through careful study that the new cultivar of the present invention exhibits the following combination of characteristics:

(a) forms on a highly floriferous basis attractive bright pink flowers with numerous flowers per shoot,
(b) exhibits a strong growth habit,
(c) exhibits a freely branching character wherein shoots generally are formed at each node,
(d) is suited for production in pots having a diameter of approximately 10.5 to 13 cm.,
(e) is amenable to the application of a growth hormone to reduce the height which otherwise would be achieved, and
(f) exhibits an extremely good keeping quality.

The new cultivar well meets the needs of the horticultural industry, and is particularly well suited for growing as an attractive ornamental potted plant.

The new cultivar has been found to undergo asexual propagation by shoot cuttings at De Lier, The Netherlands. The characteristics of the new cultivar have been found to be firmly fixed and well retained and to be strictly transmissible by such asexual propagation from one generation to another.

The new cultivar has not been observed under all possible environmental conditions to date. Accordingly, it is possible that the phenotype described herein may vary with changes in the environment such as temperature, light intensity, and day length.

The new cultivar of the present invention has been named the Kiebessy cultivar.

BRIEF DESCRIPTION OF THE PHOTOGRAPH

The accompanying photograph shows as nearly true as it is reasonably possible to make the same in a color illustration of this character, a typical specimen of the overall plant of the new cultivar wherein the attractive bright pink blossoms, growth habit, and large leaves are apparent. The plant was grown in a greenhouse at De Lier, The Netherlands, under conditions which closely approximate those generally used in commercial practice.

DETAILED DESCRIPTION

The chart used in the identification of the colors is that of The Royal Horticultural Society (R.H.S. Colour Chart). The color values were taken under artificial light conditions. Colors in common terms also are provided in some instances. These are to be accorded their usual dictionary significance. The description is based on the observation of plants grown in a greenhouse at De Lier, The Netherlands, under conditions which closely approximate those generally used in commercial practice.

Botanical classification: *Kalanchoe blossfeldiana* cv. Kiebessy.

Parengate:

*Female parent.*—Vesuvius cultivar.
*Male parent.*—FK 84-127.

Propagation: The new cultivar well holds its distinguishing characteristics through successive propagations by shoot cuttings. When operating at approximately 21° C., approximately 10 days are required for roots to form in the summer and approximately 15 days for roots to form in the winter. Large thick roots form in a quantity which commonly exceeds that usually formed by Kalanchoe plants.

Plant description:

*Form.*—Upright, medium-large size, growing and scheduling practices can produce medium-sized or larger plants. When grown in a 10.5 cm. diameter pot and a growth regulator such as Alar/B9 or Bonzi is applied, the plant commonly will assume a height of approximately 20 cm and a width of 20 cm. When grown in a 13 cm. diameter pot and a growth regulator such as Alar/B9 or Bonzi is applied, the plant commonly will assume a height of approximately 25 cm. and a width of approximately 20 cm. The use of a growth regulator is recommended so as to reduce the excessive stem length which otherwise would tend to occur.

*Growth habit.*—Strong rate of growth, generally shoots are formed at every node.

Foliage description: Leaves are simple, opposite, and generally are symmetrical.

*Leaf size.*—Average. When a flowering plant is being grown in a 10.5 cm. diameter pot, a fully grown leaf commonly is approximately 125 mm. in length and approximately 95 mm. in width.

*Leaf shape.*—Elliptic, the apex is acute to obtuse, and the base is acute.

*Leaf texture.*—Glabrous, coriaceous, succulent.

*Leaf margin.*—Crenate.

*Leaf color.*—On young foliage, the upper side is Green Group 137A and the under side is Green Group 137C. On mature foliage, the upper side is Yellow-Green Group 147A and the under side is Yellow-Green Group 147B.

Flowering description:

*Flowering habit.*—The inflorescence on each shoot is formed by dichotomous branching and starts with the opening of the terminal flower on the main axis and is followed by terminal flowers on the side branches. The opening of new buds commonly will continue over a period of weeks. Commonly individual flowers last 3 weeks or more following opening.

*Natural flowering season.*—November. Under controlled daylight at 25° C. in the summer the flowering time is approximately 9 weeks, and under controlled daylight at 20° C. in the winter the flowering time is approximately 11 weeks. The flowering duration commonly is influenced by the temperature, light intensity, and other growing conditions.

*Buds.*—Oblong and assume a tubular configuration as the petals mature, are sheathed with 4 green sepals, the corolla commonly is approximately 16 mm. in length at maturity, and the length of the bud commonly is approximately 17 mm.

*Flowers borne.*—Compound dichasial cymes are present on fairly long peducles. The peducule length is influenced by growing conditions and the application of growth hormone such as Alar/B9 or Bonzi. The peduncles commonly are up to 6 mm. in length.

*Flower quantity.*—Very floriferous with new buds continuing to develop.

*Petal shape.*—Oval with cuspidate apex.

*Petal coloration.*—Red Group 52A on the upper surface fading to Red-Purple Group 58C, and Red Group 55B, 55C and 55D on the under surface.

*Petal number.*—Four united in the corolla.

*Petal size.*—Approximately 6 to 8 mm. in length.

*Flower diameter.*—Commonly approximately 16 mm.

*Stamens.*—8 in number. The anthers are flat and elliptic in configuration. The filaments are yellow in coloration, and the pollen is yellow in coloration.

*Pistils.*—The stigmas are flat in configuration. The styles are greenish-white in coloration. The ovaries are four-celled, green in coloration, and approximately 9 mm. long.

Disease resistance: No known Kalanchoe diseases have been observed to date.

I claim:

1. A new and distinct cultivar of Kalanchoe plant characterized by the following combination of characteristics:

(a) forms on a highly floriferous basis attractive bright pink flowers with numerous flowers per shoot,
(b) exhibits a strong growth habit,
(c) exhibits a freely branching character wherein shoots generally are formed at each node,
(d) is suited for production in pots having a diameter of approixmately 10.5 to 13 cm.,
(e) is amenable to the application of a growth hormone to reduce the height which otherwise would be achieved, and
(f) exhibits an extremely good keeping quality, substantially as herein shown and described.

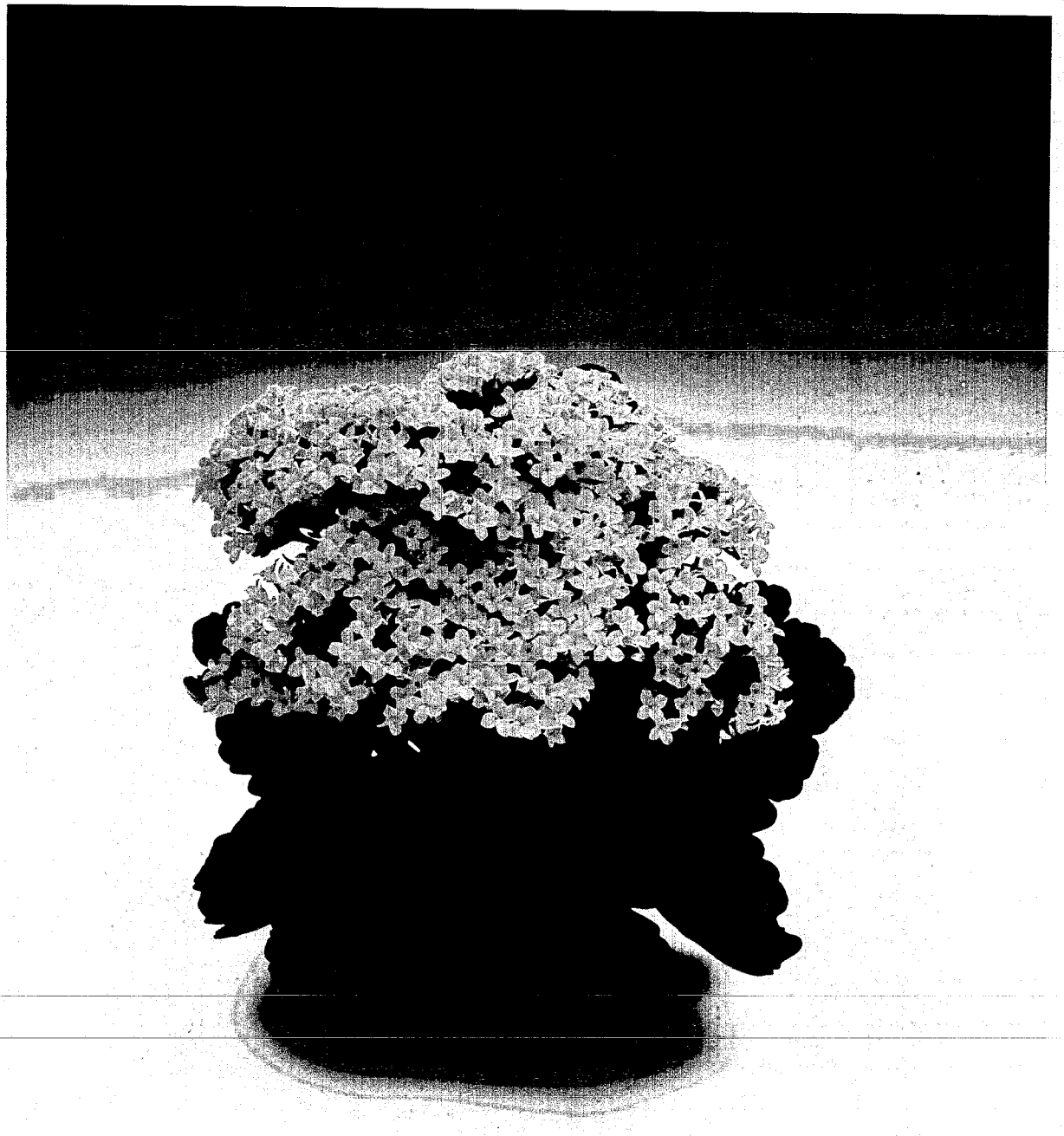

* * * * *